(12) United States Patent
Chung

(10) Patent No.: US 6,861,611 B2
(45) Date of Patent: Mar. 1, 2005

(54) WELD CHECKING APPARATUS FOR LASER WELDING MACHINE

(75) Inventor: Kweon Yong Chung, Seoul (KR)

(73) Assignee: Fasweld Inc., Seoul (KR)

( * ) Notice: Subject to any disclaimer, the term of this patent is extended or adjusted under 35 U.S.C. 154(b) by 0 days.

(21) Appl. No.: 10/622,140

(22) Filed: Jul. 18, 2003

(65) Prior Publication Data

US 2004/0124183 A1 Jul. 1, 2004

(30) Foreign Application Priority Data

Jul. 19, 2002 (KR) .................................. 10-2002-0042618

(51) Int. Cl.[7] .......................... B23K 26/20; B23K 26/03
(52) U.S. Cl. ................................................. 219/121.63
(58) Field of Search ...................... 219/121.63, 121.64, 219/121.83

(56) References Cited

U.S. PATENT DOCUMENTS 3,383,491 A * 5/1968 Muncheryan .......... 219/121.63
3,775,586 A * 11/1973 Flint et al. .............. 219/121.63

FOREIGN PATENT DOCUMENTS

| JP | 60-152386 A | * | 8/1985 |
| JP | 63-280209 A | * | 11/1988 |

* cited by examiner

*Primary Examiner*—Geoffrey S. Evans
(74) *Attorney, Agent, or Firm*—Jacobson Holman PLLC

(57) ABSTRACT

A weld checking apparatus for a laser welding machine having a welding head triggering laser beam to a welding object includes an auxiliary flash intercepting plate removably mounted on a flexible arm installed on the welding head to intercept a flash generated during a laser welding process, a weld-checking/eye-protecting glass assembly disposed on a center portion of the auxiliary flash intercepting plate to display a weld portion in an enlarged scale during the welding process while intercepting the flash by being opened and closed in synchronization with a laser beam trigger speed of the welding head, and an open/close control part for generating a trigger pulse and an open/close pulse synchronized with the trigger pulse and for providing the open/close pulse to the weld-checking/eye-protecting glass through the electric cable 50 to open and close the weld-checking/eye-protecting glass assembly.

6 Claims, 2 Drawing Sheets

WELD CHECKING APPARATUS FOR LASER WELDING MACHINE

BACKGROUND OF THE INVENTION

1. Field of the Invention

The present invention relates to a weld checking apparatus for a laser or spot welding machine, which allows a worker to check a weld state in the course of the welding process, and more particularly, to a weld checking apparatus for a welding machine that allows a worker to precisely see the weld state with the naked eye while protecting the worker's eyes from strong light such as a flash and plasma that are generated in the course of a laser or general spot welding process.

2. Description of the Related Art

Generally, there are a variety of welding methods. In recent years, among these welding methods, laser welding appears on the stage instead of spot welding.

Welding with a spot welding machine is performed with a welding head contacting a welding object in a state where electric power is applied to the welding object. However, the laser-welding machine makes it possible to realize non-contact high speed welding. The laser welding machine is designed such that a laser beam generated by an oscillator is triggered to a welding object through an output adjusting lens and a plurality of prisms in a welding head, in which the oscillator and other required parts are disposed, to perform precise welding. The output of the laser beam during the welding is adjusted by varying an angle of the output adjusting lens with respect to an advancing axis of the laser beam.

When a welding object is welded by a laser beam triggered from a non-contact type laser welding machine or by electric power applied from a contact type spot welding machine, a strong light such as a flash or plasma is generated. Particularly, since the laser welding machine performs precise welding by one or scores of beam triggers per minute, it is impossible for a worker to weld while checking the weld state with the naked eye due to the strong light of the beams.

Accordingly, in recent years, a weld checking apparatus for checking the weld state during laser welding or spot welding in an automatic production line has been developed on a commercial scale.

The weld-checking apparatus comprises a relay switch coupled to an output side, the relay switch outputting a switching signal when the laser or spot welding is performed, and a display part for displaying the number of times the welding is performed, i.e., the number of welds, by receiving a switching signal from the relay switch. Such a weld-checking apparatus is installed on a robot for performing the laser or spot welding in an automatic production line, notifying a worker only how many times the welding is performed.

That is, the weld-checking apparatus is designed to display the number of times the welding was performed whenever laser welding or spot welding is processed in an automatic production line. Therefore, it is impossible for the worker to check whether the robot is correctly welding the welding object. As a result, after a large number of welding objects are welded by the robot, the worker must examine the welded portions of the objects with the naked eye to determine if there are any bad welds. When there is bad welding on the object, it must be re-welded using the robot, which is troublesome for the worker. Furthermore, since the re-welded portion is not smooth, it may be easily damaged.

Particularly, when precise manual laser welding is required without using a robot, it is impossible for the worker to check the weld state in the course of the welding process due to a strong light such as a flash, plasma, and the like that are generated during the welding process. Therefore, the worker must check the welded portion with the naked eye after each unit welding process is finished. This must be repeated until the entire welding process is finished, deteriorating the advantage of the laser welding that can realize the non-contacting high speed welding. Furthermore, since it is impossible to check the weld state while performing the welding process, the weld is not precise and is unevenly realized.

SUMMARY OF THE INVENTION

Therefore, the present invention has been made in an effort to solve the above described problems of conventional arts.

An object of the present invention is to provide a weld-checking apparatus for a laser welding machine, which is inexpensive and allows a worker to check a weld state with the naked eye in real time.

Another object of the present invention is to provide a weld-checking apparatus for a laser welding machine, which is light and compact for mobility, while displaying the weld portion in an enlarged scale in real time.

To achieve these objects and other advantages and in accordance with the purpose of the invention, as embodied and broadly described herein, there is provided a weld checking apparatus for a laser welding machine having a welding head triggering laser beam to a welding object, the weld checking apparatus comprising an auxiliary flash intercepting plate removably mounted on a flexible arm installed on the welding head to intercept a flash generated during a laser welding process; a weld-checking/eye-protecting glass assembly disposed on a center portion of the auxiliary flash intercepting plate to display a weld portion in an enlarged scale during the welding process while intercepting the flash by being opened and closed in synchronization with a laser beam trigger speed of the welding head; and open/close control means for generating a trigger pulse and an open/close pulse synchronized with the trigger pulse and for providing the open/close pulse to the weld-checking/eye-protecting glass through the electric cable 50 to open and close the weld-checking/eye-protecting glass assembly.

Preferably, the weld-checking/eye-protecting glass assembly comprises upper and lower protecting glasses coupled to and projected upward and downward from top and bottom surfaces of the auxiliary flash intercepting plate, respectively; a magnifying glass 43 coupled on the lower protecting glass to magnify a weld portion; a filter lens disposed above the magnifying glass and coated with a reflecting member to intercept a harmful wave that is generated during the welding process, by reflecting the harmful wave; and an LCD shutter disposed between the upper protecting glass and the filter lens to display the weld portion in real time while being closed and opened by the open/close pulse generated from the open/close control means.

Further preferably, the open/close control means comprises a trigger switch for generating a welding start signal; an electric power controller for generating operation electric power in response to the welding start signal; a micro processor for controlling an overall system operation using voltage supplied from the electric power controller; a pulse signal generator controlled by the microprocessor to generate a pulse; an oscillating lamp power part, oscillated by the electric power and the pulse respectively supplied from the electric power controller and the pulse signal generator, for generating a trigger pulse for triggering a laser beam and outputting the triggering pulse through an output terminal; and a shutter synchronization-driving power part 76 for generating an open/close pulse signal synchronized with the trigger pulse generated by the oscillating lamp power part and providing the open/close pulse signal to the LCD shutter of the weld-checking/eye-protecting glass assembly.

Selectively, the closing time of the open/close signal is set to be longer than the width of the trigger pulse.

Preferably, when the width of the trigger pulse is in a range of 0.5–20 ms, the closing time is set to 30 ms.

Therefore, in the present invention, as a strong flash is obstructed by closing the LCD shutter in response to the signal synchronized with the beam trigger speed at each unit welding process and the LCD shutter is opened whenever the unit welding process is finished, it becomes possible to check the weld state during the overall welding process in real time while protecting the worker's eyes.

As a result, precise welding is possible even for manual welding, and weld quality is improved. In addition, the present invention has a further advantage of obtaining safety for the use of the laser beam by obstructing the strong flash, while making it possible for the worker to check the weld state in real time.

It is to be understood that both the foregoing general description and the following detailed description of the present invention are exemplary and explanatory and are intended to provide further explanation of the present invention as claimed.

BRIEF DESCRIPTION OF THE DRAWINGS

The accompanying drawings, which are included to provide a further understanding of the present invention and are incorporated in and constitute a part of this application, illustrate embodiment(s) of the present invention and together with the description serve to explain the principle of the present invention. In the drawings.

DETAILED DESCRIPTION OF THE PREFERRED EMBODIMENTS

Reference will now be made in detail to a preferred embodiment of the present invention with reference to the accompanying drawings.

Figure 1:
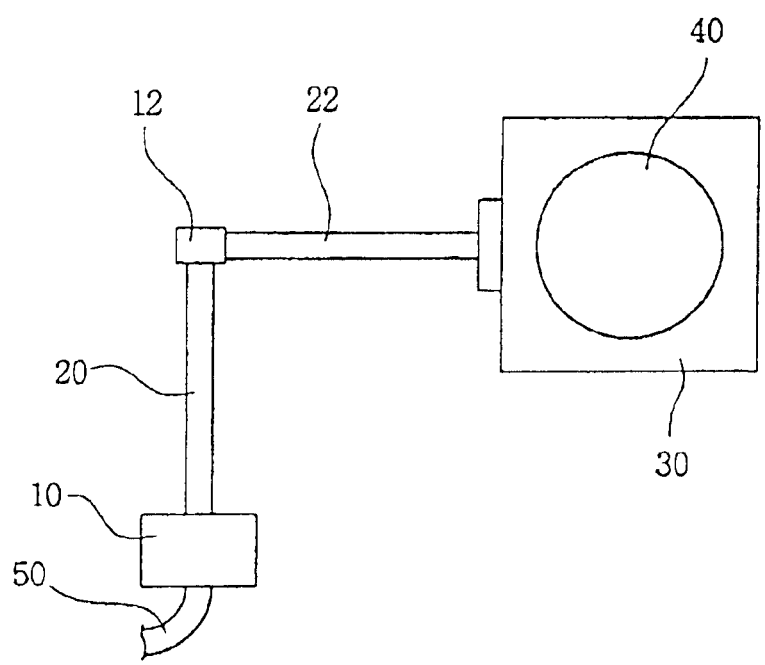
FIG. 1 is a plan view of a weld-checking apparatus, which is mounted on a flexible arm of a laser welding machine, according to a preferred embodiment of the present invention.
Figure 2:
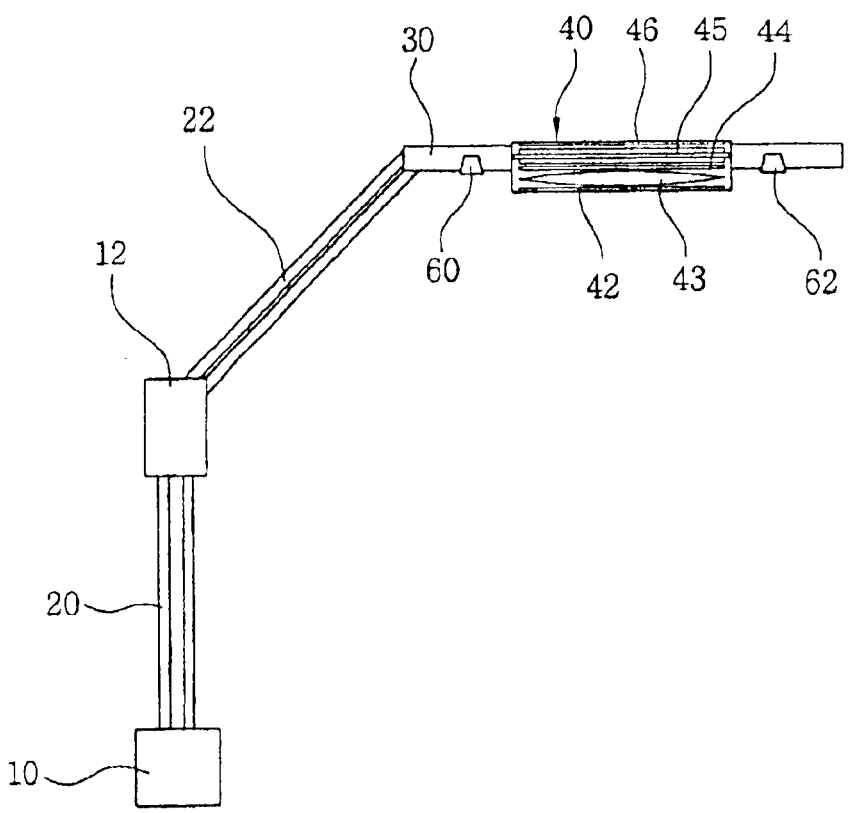
FIG. 2 is a schematic side view of a weld-checking apparatus for a laser welding machine depicted in FIG. 1.
Figure 3:
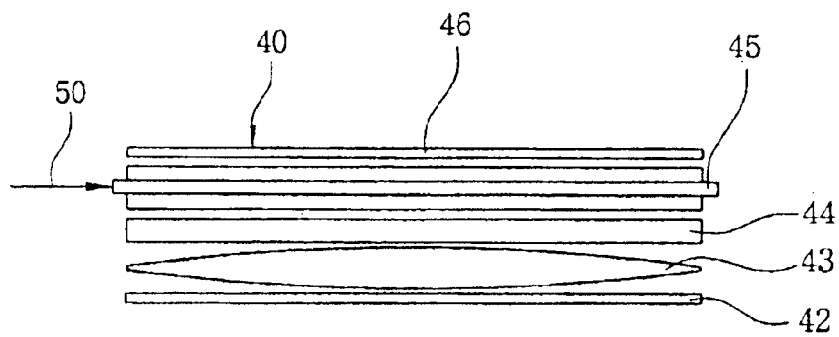
FIG. 3 is an enlarged side view of a weld-checking/eye-protecting glass assembly depicted in FIG. 2.

FIG. 1 shows a plan view of a weld-checking apparatus, which is mounted on a flexible arm of a laser welding machine, according to a preferred embodiment of the present invention, FIG. 2 shows a schematic side view of a weld-checking apparatus for a laser welding machine depicted in FIG. 1, and FIG. 3 shows an enlarged sectional view of a weld-checking apparatus depicted in FIG. 2.

As shown in the drawings, the inventive weld-checking apparatus for a laser welding machine comprises a magnetic member 10 removably mounted on a welding head (not shown), a first flexible arm 20, a first end of which is vertically fixed on the magnetic member 10, receiving an electric cable 50, a second flexible arm 22 articulately connected to the first flexible arm 20 and receiving the electric cable 50, an articular support 12 disposed between the first and second flexible arms 20 and 22 for the articulating motion of the second flexible arm 22 with respect to the first flexible arm 20, an auxiliary flash intercepting plate 30 for intercepting a flash generated during a laser welding process, first and second lights 60 and 62 mounted on both sides of a bottom surface of the auxiliary flash intercepting plate 30 to illuminate light using electric power supplied through the electric cable 50, a weld-checking/eye-protecting glass assembly 40 disposed on a center portion of the auxiliary flash intercepting plate 30 to display a weld portion in an enlarged scale during the welding process while intercepting the flash by being opened and closed in synchronization with a laser beam trigger speed of the welding head, and an open/close control part for generating a trigger pulse and an open/close pulse synchronized with the trigger pulse and for providing the open/close pulse to the weld-checking/eye-protecting glass 40 through the electric cable 50 to open and close the weld-checking/eye-protecting glass assembly 40. The auxiliary flash intercepting plate 30 is square-shaped. The open/close control part will be described in more detail with reference to FIG. 4 herein below.

As shown in FIGS. 2 and 3, the weld-checking/eye-protecting glass assembly 40 comprises upper and lower protecting glasses 42 and 46 coupled to and projected upward and downward from top and bottom surfaces of the auxiliary flash intercepting plate 30, respectively, a magnifying glass 43 coupled on the lower protecting glass 42 to magnifying a weld portion, a filter lens 44 disposed above the magnifying glass 43 and coated with a reflecting member to intercept a harmful wave that is generated during the welding process, by reflecting the same, and an LCD shutter 45 disposed between the upper protecting glass 46 and the filter lens 44 to display the weld portion in real time while being closed and opened by the open/close pulse input through the cable 50.

Figure 4:
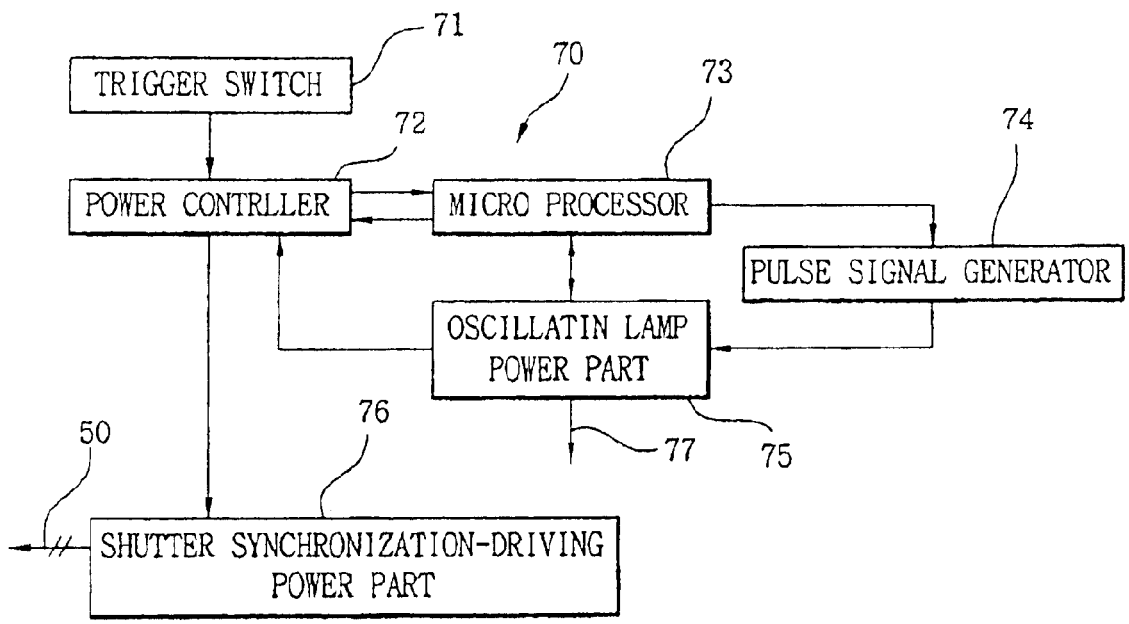
FIG. 4 is a block diagram illustrating a control part for controlling a drive of an LCD shutter in response to a laser beam trigger according to a preferred embodiment of the present invention.

As shown in FIG. 4, the open/close control part 70 comprises a trigger switch 71 for generating a welding start signal in accordance with the manipulation of a worker, an electric power controller 72 for generating operation electric power in response to the welding start signal, a micro processor 73 for controlling an overall system operation by the operation electric power supplied from the electric power controller 72, a pulse signal generator 74 controlled by the microprocessor 73 to generate a pulse having a predetermined period, an oscillating lamp power part 77, oscillated by the electric power and the pulse respectively supplied from the electric power controller 72 and the pulse signal generator 74, for generating a trigger pulse for triggering a laser beam and outputting the triggering pulse through an output terminal 77, and a shutter synchronization-driving power part 76 for generating an open/close pulse signal synchronized with the trigger pulse generated by the oscillating lamp power part 77 and providing the open/close pulse signal to the LCD shutter 45 of the weld-checking/eye-protecting glass assembly 40 through the electric cable 50 received in the first and second flexible arms 20 and 22.

The operation of the above-described weld-checking apparatus for the laser welding machine will be described in more detail with reference to FIGS. 1 to 5.

First, when the worker manipulates the trigger switch 71 after approaching the welding head to a welding object and setting the auxiliary flash intercepting plate 30 and the weld-checking/eye-protecting glass assembly 40 toward a weld portion of the welding object by adjusting the first and second flexible arms 20 and 22 coupled on the magnetic member 10 and the articular support 12, the electric power controller 72 generates the operation electric power and supplies the same to the microprocessor 73.

The microprocessor 73 receiving the operation electric power from the electric power controller 72 controls the oscillating lamp power part 75 and the pulse signal generator 74 such that the pulse signal generator 74 generates a pulse having a predetermined period and transmits the same to the oscillating lamp power part 75.

Figure 5:
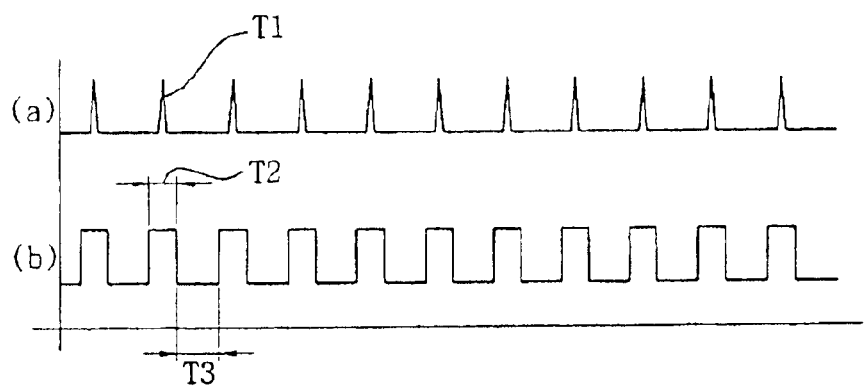
FIG. 5 is an output wave diagram illustrating a synchronizing pulse of a laser beam trigger and an LCD shutter.

The oscillating lamp power part 75 is driven by the operation electric power from the electric power controller 72 and is oscillated in accordance with the pulse transmitted from the pulse signal generator 74, thereby generating a trigger pulse (a) as shown in FIG. 5. The trigger pulse (a) is transmitted to the welding head through the output terminal 77 to allow the welding head to trigger a laser beam, while controlling the electric power controller 72. Here, a width T1 (a flash generating time) of the trigger pulse (a) is preferably set to be in a range of about 0.5–20 ms.

The electric power controller 72 controls the shutter synchronization-driving power part 76 in response to the trigger pulse T1 transmitted from the oscillating lamp power part 75 such that the shutter synchronization-driving power part 76 generates an open/close pulse signal (b) synchronized with the trigger pulse T1 as shown in FIG. 5, and transmits the same to the LCD shutter 45 of the weld-checking/eye-protecting glass assembly 40. Here, the closing time T2 of the open/close signal for closing and opening the LCD shutter 45 is preferably set to be longer than the laser beam triggering speed (the width of the pulse: ms). For example, when the width T1 of the trigger pulse generated from the oscillating lamp power part 75 is in a range of 0.5–20 ms, the closing time T2 of the open/close pulse signal generated from the shutter synchronization-driving power part 76 is preferably set to more than 30 ms.

Meanwhile, when the laser beam is triggered to the welding object from the welding head by the trigger pulse generated from the oscillating lamp power part 75, strong light such as a flash and plasma is secondly generated together with welding fragments. At this point, the strong light and fragments are blocked by the auxiliary flash intercepting plate 30 as well as by the lower protecting glass 42 of the weld-checking/eye-protecting glass assembly 40. In addition, as the LCD shutter 45 of the weld-checking/eye-protecting glass assembly 40 is opened and closed in response to the closing time T2 and an opening time T3 of the open/close pulse signal, it becomes possible for the worker to check the weld state of the weld portion through the weld-checking/eye-protecting glass assembly 40. That is, when the worker intends to check the weld state with the naked eye through the weld-checking/eye-protecting glass assembly 40, the magnifying glass 43 located above the lower protecting glass 42 displays the weld portion in an enlarged scale, and the filter lens 44 reflects a harmful light wave (1064 nm) generated during the welding, marking, and cutting processes, and displays the magnified weld portion on the upper protecting glass 46 through the LCD shutter 45. At this point, as described above, the LCD shutter 45 is opened and closed in response to the closing and opening times T2 and T3 of the open/close pulse signal synchronized with the trigger pulse (T1: the laser beam trigger speed). Therefore, when the LCD shutter 45 is closed, the strong flash is obstructed, and when opened, the weld state is displayed through the upper protecting glass 46, thereby making it possible for the worker to check the weld state in real time. During this procedure, the lights 60 and 62 illuminate light to the weld portion using the electric power supplied through the cable 50.

As described above, in the prior art, the weld-checking is possible only when the overall welding process is finished. However, in the present invention, as the strong flash is obstructed by closing the LCD shutter in response to the signal synchronized with the beam trigger speed at each unit welding process and the LCD shutter is opened whenever the unit welding process is finished, it becomes possible to check the weld state during the overall welding process in real time while protecting the worker's eyes.

As a result, precise welding is possible even for manual welding, and the weld quality is improved. In addition, the present invention has a further advantage of obtaining safety for the use of the laser beam by obstructing the strong flash, while making it possible for the worker to check the weld state in real time.

The forgoing embodiment is merely exemplary and is not to be construed as limiting the present invention. The present teachings can be readily applied to other types of apparatus. The description of the present invention is intended to be illustrative, and not to limit the scope of the claims. Many alternatives, modifications, and variations will be apparent to those skilled in the art.

What is claimed is:

1. A weld checking apparatus for a laser welding machine having a welding head triggering laser beam to a welding object, the weld checking apparatus comprising:
   an auxiliary flash intercepting plate removably mounted on a flexible arm installed on the welding head to intercept a flash generated during a laser welding process;
   a weld-checking/eye-protecting glass assembly disposed on a center portion of the auxiliary flash intercepting plate to display a weld portion in an enlarged scale during the welding process while intercepting the flash by being opened and closed in synchronization with a laser beam trigger speed of the welding head; and
   open/close control means for generating a trigger pulse and an open/close pulse synchronized with the trigger pulse and for providing the open/close pulse to the weld-checking/eye-protecting glass through the electric cable (50) to open and close the weld-checking/eye-protecting glass assembly.

2. The weld checking apparatus of claim 1, wherein the weld-checking/eye-protecting glass assembly comprises:
   upper and lower protecting glasses coupled to and projected upward and downward from top and bottom surfaces of the auxiliary flash intercepting plate, respectively;
   a magnifying glass 43 coupled on the lower protecting glass to magnifying a weld portion;
   a filter lens disposed above the magnifying glass and coated with a reflecting member to intercept a harmful wave that is generated during the welding process, by reflecting the harmful wave; and an LCD shutter disposed between the upper protecting glass and the filter lens to display the weld portion in real time while being closed and opened by the open/close pulse generated from the open/close control means.

3. The weld checking apparatus of claim 1, wherein the open/close control means comprises:

a trigger switch for generating a welding start signal;

an electric power controller for generating operation electric power in response to the welding start signal;

a micro processor for controlling an overall system operation using a voltage supplied from the electric power controller;

a pulse signal generator controlled by the microprocessor to generate a pulse;

an oscillating lamp power part, oscillated by the electric power and the pulse respectively supplied from the electric power controller and the pulse signal generator, for generating a trigger pulse for triggering a laser beam and outputting the triggering pulse through an output terminal; and a shutter synchronization-driving power part (76) for generating an open/close pulse signal synchronized with the trigger pulse generated by the oscillating lamp power part and providing the open/close pulse signal to the LCD shutter of the weld-checking/eye-protecting glass assembly.

4. The weld checking apparatus of claim 1, wherein the closing time of the open/close signal is set to be longer than a width of the trigger pulse.

5. The weld checking apparatus of claim 4, when the width of the trigger pulse is in a range of 0.5–20 ms, the closing time is set to 30 ms.

6. The weld checking apparatus of claim 1 further comprising a light installed on a bottom of the auxiliary flash intercepting plate to illuminate light to the weld portion during welding and weld-checking.

* * * * *